(12) United States Patent
Richard (10) Patent No.: US 9,974,540 B2
(45) Date of Patent: May 22, 2018

(54) ADAPTER DIRECT DRIVE TWIST-LOCK RETENTION MECHANISM

(71) Applicant: Covidien LP, Mansfield, MA (US)

(72) Inventor: Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 277 days.

(21) Appl. No.: 14/467,100

(22) Filed: Aug. 25, 2014

(65) Prior Publication Data

US 2015/0112381 A1    Apr. 23, 2015

Related U.S. Application Data

(60) Provisional application No. 61/892,682, filed on Oct. 18, 2013.

(51) Int. Cl.
*A61B 17/28* (2006.01)
*A61B 17/072* (2006.01)
*A61B 17/00* (2006.01)

(52) U.S. Cl.
CPC .......... *A61B 17/07207* (2013.01); *A61B 2017/0046* (2013.01); *A61B 2017/00473* (2013.01); *A61B 2017/00486* (2013.01)

(58) Field of Classification Search
CPC .......... A61B 17/07207; A61B 17/0046; A61B 2017/00473; A61B 2017/00486
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

Extended European Search Report corresponding to International Application No. EP 15 15 1076.5 dated Apr. 22, 2015.

(Continued)

*Primary Examiner* — Julie A Szpira (57) ABSTRACT

A surgical device adapter for coupling an end effector to a handle assembly is disclosed. The surgical device adapter includes: a housing including a proximal end couplable to a distal end of a handle assembly; and a drive coupling assembly and selectively couplable to the handle assembly, the drive coupling assembly including a tubular clamping member having at least one flexible member, the tubular clamping member movable from a proximal position in which the at least one flexible member is disengaged from the distal end of the handle assembly to a distal position in which the at least one flexible member is engaged to the distal end of the handle assembly.

13 Claims, 3 Drawing Sheets

(56) References Cited

U.S. PATENT DOCUMENTS

| | | |
|---|---|---|
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,947,996 A * | 9/1999 | Logeman ............... A61B 17/29 600/564 |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B2 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |

(56) References Cited

U.S. PATENT DOCUMENTS

| | | |
|---|---|---|
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,021,321 B2 * | 9/2011 | Zawacki ............ A61M 1/3653 604/29 |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |

(56) References Cited

U.S. PATENT DOCUMENTS

| | | |
|---|---|---|
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0095070 A1* | 4/2011 | Patel .................. A61B 17/115 227/181.1 |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1* | 4/2012 | Zemlok ............ A61B 17/07207 606/1 |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0138129 A1* | 5/2013 | Garrison ............ A61B 18/1445 606/170 |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A2 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1 813 203 A2 | 8/2007 |
| EP | 1813199 A1 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2316354 A2 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2599447 A2 | 6/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08-038488 | 2/1996 |
| JP | 2005-125075 A | 5/2005 |
| KR | 20120022521 A | 3/2012 |

(56) References Cited

FOREIGN PATENT DOCUMENTS

| WO | 99/15086 | A1 | 4/1999 |
|---|---|---|---|
| WO | 2000/072760 | A1 | 12/2000 |
| WO | 2000/072765 | A1 | 12/2000 |
| WO | 2003/000138 | A2 | 1/2003 |
| WO | 2003/026511 | A1 | 4/2003 |
| WO | 2003/030743 | A2 | 4/2003 |
| WO | 2003065916 | A1 | 8/2003 |
| WO | 2003/077769 | A1 | 9/2003 |
| WO | 2003090630 | A2 | 11/2003 |
| WO | 2004/107989 | A1 | 12/2004 |
| WO | 2006/042210 | A2 | 4/2006 |
| WO | 2007016290 | A2 | 2/2007 |
| WO | 2007/026354 | A1 | 3/2007 |
| WO | 2007137304 | A2 | 11/2007 |
| WO | 2008/131362 | A2 | 10/2008 |
| WO | 2008/133956 | A2 | 11/2008 |
| WO | 2009039506 | A1 | 3/2009 |
| WO | 2007014355 | A3 | 4/2009 |
| WO | 2009/132359 | A2 | 10/2009 |
| WO | 2009/143092 | A1 | 11/2009 |
| WO | 2009149234 | A1 | 12/2009 |
| WO | 2011/108840 | A2 | 9/2011 |
| WO | 2012040984 | A1 | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report for EP Application No. 14189358.6 dated Jul. 8, 2015.
Chinese Office Action dated Dec. 25, 2017 issued in corresponding Chinese Application No. 2014105599175.

* cited by examiner

ADAPTER DIRECT DRIVE TWIST-LOCK RETENTION MECHANISM

CROSS-REFERENCE TO RELATED APPLICATIONS

This application claims the benefit of and priority to U.S. Provisional Patent Application No. 61/892,682, filed Oct. 18, 2013, the entire disclosure of which is incorporated by reference herein

BACKGROUND

1. Technical Field

The present disclosure relates to surgical apparatuses, devices and/or systems for performing endoscopic surgical procedures and methods of use thereof. More specifically, the present disclosure relates to electromechanical handheld surgical apparatuses, adapters, devices and/or systems configured for use with removable disposable loading units and/or single use loading units for clamping, cutting and/or stapling tissue.

2. Background of Related Art

Currently there are various drive systems for operating and/or manipulating electromechanical surgical devices. In many instances the electromechanical surgical devices include a reusable handle assembly, and disposable or single-use loading units. The loading units are selectively connected to the handle assembly prior to use and then disconnected from the handle assembly following use in order to be disposed of or in some instances sterilized for re-use.

Many of the existing end effectors for use with many of the existing surgical devices and/or handle assemblies are driven by a linear force. For example, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use rotary motion to deliver power or the like.

In order to make the linear driven end effectors compatible with surgical devices and/or handle assemblies that use a rotary motion to deliver power, a need exists for adapters and/or adapter assemblies to interface between and interconnect the linear driven end effectors with the rotary driven surgical devices and/or handle assemblies. There is also a need for adapters that include manual retraction, connection, and locking and release mechanisms for coupling to the surgical devices.

SUMMARY

Further details and aspects of exemplary embodiments of the present invention are described in more detail below with reference to the appended Figures.

According to one embodiment of the present disclosure, a surgical device adapter for coupling an end effector to a handle assembly is disclosed. The surgical device adapter includes: a housing including a proximal end couplable to a distal end of a handle assembly; and a drive coupling assembly and selectively couplable to the handle assembly, the drive coupling assembly including a tubular clamping member having at least one flexible member, the tubular clamping member movable from a proximal position in which the at least one flexible member is disengaged from the distal end of the handle assembly to a distal position in which the at least one flexible member is engaged to the distal end of the handle assembly.

According to another embodiment of the present disclosure, a surgical device is disclosed. The surgical device includes: an end effector including a first jaw and a second jaw moveable relative to the first jaw; a handle assembly including at least one motor mechanically coupled to the jaw assembly; and an adapter assembly removably coupled to a proximal end of the jaw assembly and a distal end of the handle assembly. The adapter assembly includes: a housing including a proximal end couplable to the distal end of the handle assembly; and a drive coupling assembly and selectively couplable to the handle assembly, the drive coupling assembly including a tubular clamping member having at least one flexible member, the tubular clamping member movable from a proximal position in which the at least one flexible member is disengaged from the distal end of the handle assembly to a distal position in which the at least one flexible member is engaged to the distal end of the handle assembly.

According to one aspect of any of the above embodiment, the surgical device adapter further includes a drive mechanism disposed within the housing and couplable to the handle assembly and the end effector.

According to another aspect of any of the above embodiments, the drive coupling assembly further includes an outer tubular member disposed over the tubular clamping member and rotatable relative thereto to move the tubular clamping member between the proximal and distal positions.

The housing may include a connector assembly and the tubular clamping member is disposed over the connector assembly.

The connector assembly may include at least one longitudinal slot defined in an outer surface thereof, the at least one longitudinal slot configured and dimensioned to interface with at least one first pin projecting from the tubular clamping member.

According to one aspect of any of the above embodiments, the tubular clamping member includes at least one cam slot configured and dimensioned to interface with at least one second pin projecting from the outer tubular member. Rotational movement of the outer tubular member translates the at least one second pin through that at least one cam slot to move the tubular clamping member between the proximal and distal positions.

According to another aspect of any of the above embodiments, the at least one flexible member includes a proximally-facing ramp surface configured to flex the at least one flexible member upon contacting a lip disposed at the distal end of the handle assembly.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left and right sides, respectively, from the perspective of the user facing the distal end of the electromechanical surgical system, apparatus and/or device from the proximal end while the surgical system, apparatus and/or device is oriented in non-rotational (e.g., home) configuration.

Figure 1:
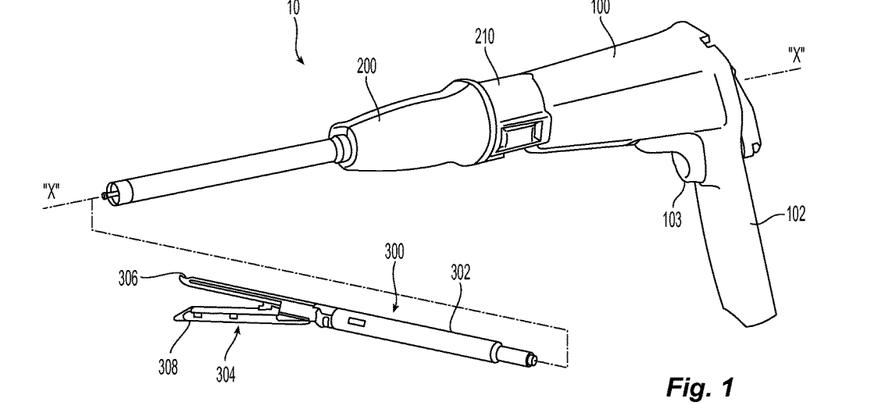
FIG. 1 is a perspective view of an electromechanical surgical system including a surgical instrument, an end effector and an adapter assembly according to the present disclosure.
Figure 2:
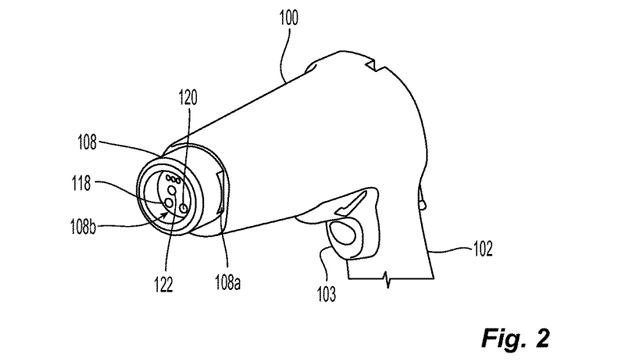
FIG. 2 is a perspective, front partial view of the surgical instrument of FIG. 1, according to the present disclosure.
Figure 3:
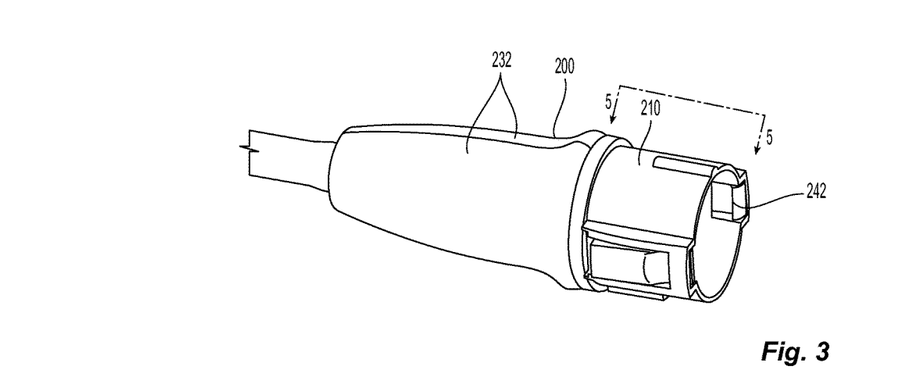
FIG. 3 is a perspective, rear view of the adapter assembly of FIG. 1, according to the present disclosure.

Referring initially to FIGS. 1-3, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 300, via an adapter assembly 200 (e.g., elongated body). The end effector 300 and the adapter assembly 200 are configured for actuation and manipulation by the electromechanical, hand-held, powered surgical instrument 100. In particular, the surgical instrument 100, the adapter assembly 200, and the end effector 300 are separable from each other such that the surgical instrument 100 is configured for selective connection with adapter assembly 200, and, in turn, adapter assembly 200 is configured for selective connection with any one of a plurality of different end effectors 300.

Reference may be made to International Application No. PCT/US2008/077249, filed Sep. 22, 2008 (Inter. Pub. No. WO 2009/039506) and U.S. Patent Application Publication No. 2011/0121049, the entire contents of all of which are incorporated herein by reference, for a detailed description of the construction and operation of exemplary electromechanical, hand-held, powered surgical instrument 100.

As illustrated in FIGS. 1 and 2, surgical instrument 100 includes a handle housing 102 including one or more controllers, a power source, and a drive mechanism having one or more motors, gear selector boxes, gearing mechanisms, and the like. The housing 102 also supports a control assembly 103. Control assembly 103 may include one or more finger-actuated control buttons, rocker devices, joystick or other directional controls, whose input is transferred to the drive mechanism to actuation the adapter assembly 200 and the end effector 300.

In particular, drive mechanism is configured to drive shafts and/or gear components in order to selectively move a tool assembly 304 of end effector 300 relative to proximal body portion 302 of end effector 300, to rotate end effector 300 about a longitudinal axis "X-X" (FIG. 1) defined by the adapter assembly 200 relative to handle housing 102, to move an anvil assembly 306 relative to a cartridge assembly 308 of end effector 300, and/or to fire a stapling and cutting cartridge within cartridge assembly 308 of end effector 300.

With continued reference to FIG. 2, the housing 102 defines a nose or connecting portion 108 configured to accept a corresponding drive coupling assembly 210 of adapter assembly 200. The connecting portion 108 of surgical instrument 100 has a cylindrical recess 108b that receives a connector assembly 240 of the drive coupling assembly 210 when adapter assembly 200 is mated to surgical instrument 100. Connecting portion 108 houses one or more rotatable drive connectors that interface with corresponding rotatable connector sleeves of the adapter assembly 200, as described in further detail below. The surgical instrument 100 includes rotatable drive connector 118, 120, 122 disposed within the connecting portion 108 that are actuated by the drive mechanism thereof (not shown).

Figure 4:
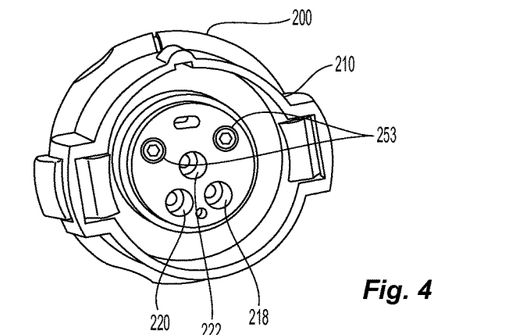
FIG. 4 is a further, perspective rear view of the adapter assembly of FIG. 1, according to the present disclosure.

With reference to FIGS. 2 and 4, when adapter assembly 200 is mated to surgical instrument 100, each of rotatable drive connectors 118, 120, 122 of surgical instrument 100 couples with a corresponding rotatable connector sleeve 218, 220, 222 of adapter assembly 200. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter assembly 200.

The mating of drive connectors 118, 120, 122 of surgical instrument 100 with connector sleeves 218, 220, 222 of adapter assembly 200 allows rotational forces to be independently transmitted via each of the three respective connector interfaces. The drive connectors 118, 120, 122 of surgical instrument 100 are configured to be independently rotated by drive mechanism.

Since each of drive connectors 118, 120, 122 of surgical instrument 100 has a keyed and/or substantially non-rotatable interface with respective connector sleeves 218, 220, 222 of adapter assembly 200, when adapter assembly 200 is coupled to surgical instrument 100, rotational force(s) are selectively transferred from drive mechanism of surgical instrument 100 to adapter assembly 200.

The selective rotation of drive connector(s) 118, 120 and/or 122 of surgical instrument 100 allows surgical instrument 100 to selectively actuate different functions of end effector 300. As discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 about an articulation axis that is transverse to longitudinal axis "X-X" (FIG. 1). In particular, the end effector 300 defines a second longitudinal axis and is movable from a first position in which the second longitudinal axis is substantially aligned with the first longitudinal axis "X-X" to at least a second position in which the second longitudinal axis is disposed at a non-zero angle with respect to the first longitudinal axis "X-X." Additionally, the selective and independent rotation of third drive connector 122 of surgical instrument 100 corresponds to the selective and independent rotation of end effector 300 about longitudinal axis "X-X" (FIG. 1) relative to handle housing 102 of surgical instrument 100.

In embodiments, adapter assembly 200 may include first, second, and third drive transmitting/converting assemblies (not shown). Reference may be made to a commonly-owned U.S. patent application Ser. No. 13/875,571, entitled, "Hand Held Surgical Handle Assembly, Surgical Adapters For Use Between Surgical Handle Assembly and Surgical End Effectors, and Methods Of Use," which describes construction and operation of exemplary first, second, and third transmitting/converting assemblies, the entire contents of which are incorporated by reference herein.

Figure 5:
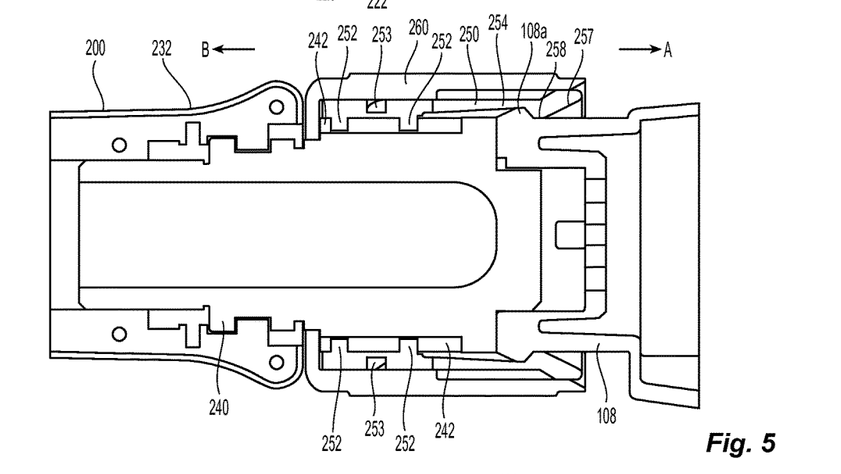
FIG. 5 is a cross-sectional, side view of a drive coupling assembly of the adapter assembly of FIG. 1 taken along section line 5-5 of FIG. 3, according to the present disclosure.
Figure 6:
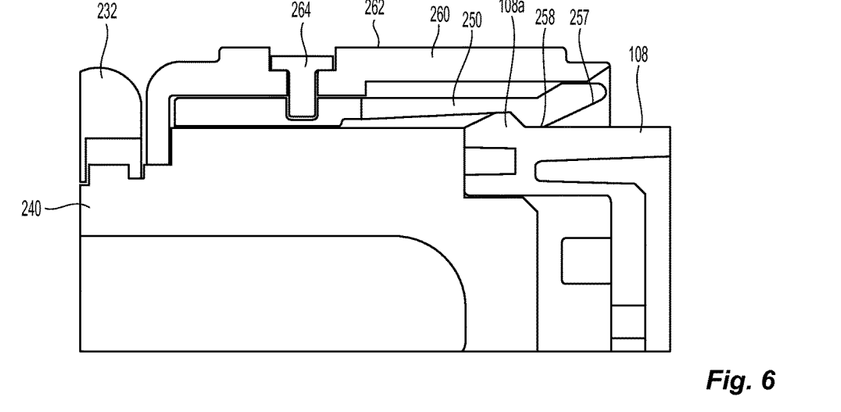
FIG. 6 is an enlarged, cross-sectional, side view of the drive coupling assembly of FIG. 5, according to the present disclosure.

With reference to FIGS. 3 and 4, the adapter assembly 200 also includes an adapter housing 232 coupled to the coupling assembly 210 and enclosing a drive mechanism (not shown). The adapter assembly 200 also includes the connector assembly 240 disposed within the coupling assembly 210, as shown in FIGS. 4-6. The connector assembly 240 is coupled to the adapter housing 232 via fasteners 233 (FIG. 4). The connector assembly 240 is configured and dimensioned to be inserted into the cylindrical recess 108b of the connector portion 108.

With reference to FIGS. 5-8, the drive coupling assembly 210 includes a clamping member 250 configured to circumferentially clamp about a lip 108a of the connecting portion 108 of the surgical instrument 100. The clamping member 250 has a tubular structure and is disposed over connector assembly 240. The connector assembly 240 includes one or more longitudinal slots 242 (FIG. 5) defined in an outer surface thereof, which are configured and dimensioned to interface with one or more pins 252 (FIGS. 5 and 7) disposed on an inner surface of the clamping member 250. The interface between the pins 252 and the corresponding slots 242 prevents rotational movement of clamping member 250 about the axis "X-X" allowing only for longitudinal movement thereof for securing (e.g., clamping) the adapter assembly 200 to the surgical instrument 100, as described in further detail below.

Figure 7:
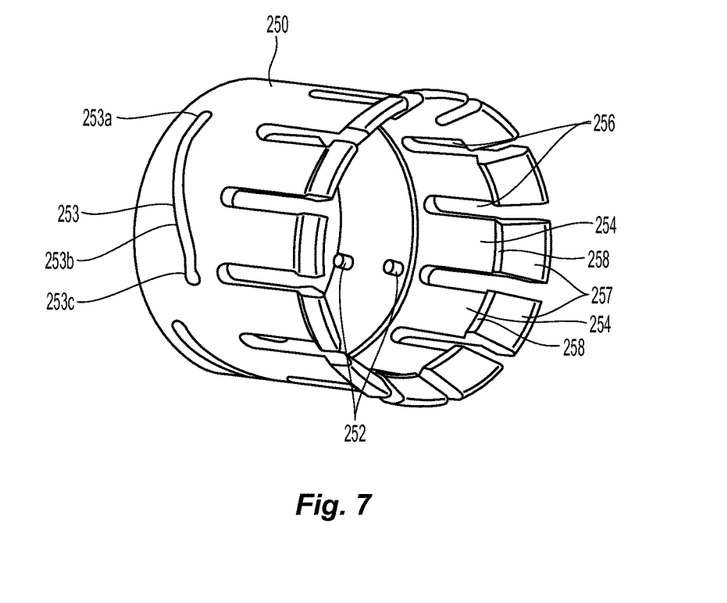
FIG. 7 is a perspective view of a tubular clamping member of the drive coupling assembly of FIG. 5, according to the present disclosure.

With reference to FIGS. 5-7, the clamping member 250 also includes a plurality of flexible members (e.g., fingers) 254 (FIG. 7) at a proximal end thereof. The flexible members 254 are configured and dimensioned to circumferentially clamp about the lip 108a of the connecting portion 108 as the clamping member 250 is moved in a proximal direction "A" and to release the lip 108a as the clamping member 250 is moved in a distal direction "B." The clamping member 250 may be formed from any resilient but flexible material, including but not limited to, metals, thermoplastics, and the like. The flexible members 254 may be produced by forming a plurality of longitudinal slots 256 (FIG. 7) within the clamping member 250 by any suitable method including, but not limited to, machining (e.g., cutting), injection molding, and the like.

Each of the flexible members 254 includes a distally-facing ramp surface 257 having a ridge 258 defined proximally thereof. This configuration allows for the members 254 to bend radially outward as the clamping member 250 is slid over of the lip 108a of the connecting portion 108 and to snap back to the unflexed configuration once the ridge 258 is moved proximally of the lip 108a. In the clamped configuration, the ridge 258 rests proximally of the lip 108a thereby coupling the adapter assembly 200 to the surgical instrument 100.

Figure 8:
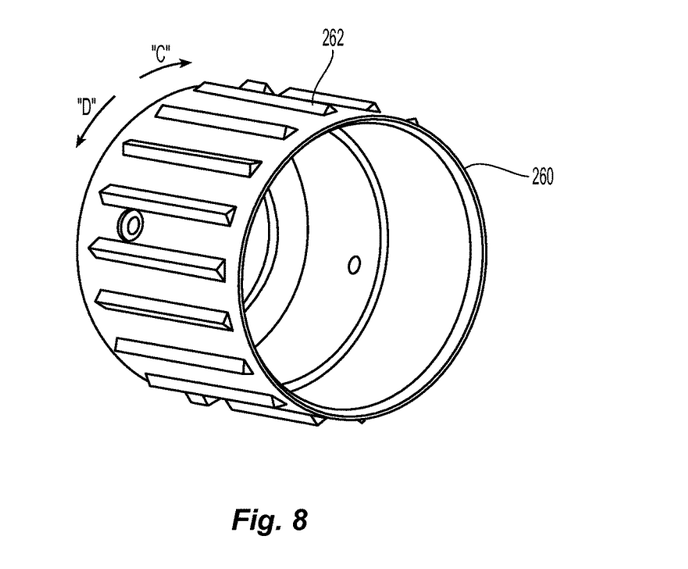
FIG. 8 is a perspective view of an outer tubular member of the drive coupling assembly of FIG. 5, according to the present disclosure.

Longitudinal movement of the clamping member 250 is accomplished via an outer tubular member 260, as shown in FIGS. 5, 6, and 8. In particular, the outer member 260 is actuated by the user to engage and/or disengage the clamping member 250 from the lip 108a of the connecting portion 108. The outer member 260 has a tubular structure and is disposed over the clamping member 250. The outer member 260 includes a textured surface 262 disposed on an outer surface thereof to provide for enhanced grip by the user. The outer member 260 also includes one or more pins 264 (FIG. 6) configured and dimensioned to interface with one or more corresponding cam slots 253 (FIGS. 5-7) defined within a proximal portion of the clamping member 250. The cam slots 253 of clamping member 250 are oriented transverse to the longitudinal axis "X-X." Each of the cam slots 253 includes a clamped resting portion 253a, a ramp portion 253b, and an unclamped resting portion 253c. The resting portions 253a and 253c of the cam slot 253 allow for the pin 264 to securedly remain within the cam slot 253, such that the clamping member 250 does not revert to either unclamped or clamped configuration without external forces (e.g., user actuation or rotation of outer member 260).

To attach the adapter assembly 200 to the surgical instrument 100, the drive coupling assembly 210 is placed in an unclamped configuration in which the clamping member 250 is in a proximal position. In the unclamped configuration, outer member 260 of drive coupling assembly 210 is rotated to the unclamped configuration, such that flexible members 254 project proximally from outer member 260 and are not bound by outer member 260 and are thus free to deflect radially outward.

The adapter assembly 200 is approximated to the surgical instrument 100 such that the connector assembly 240 is inserted into the connecting portion 108. As the connection portion 108 is inserted into the drive coupling assembly 210, the clamping member 250 is slid over the lip 108a of the connecting portion 108 and subsequently snaps over the lip 108a back to the unflexed configuration once the ridges 258 of the flexible members 254 move proximally of the lip 108a.

Once the adapter assembly 200 is mated to the surgical instrument 100, the outer member 260 is rotated in a first direction (e.g., clockwise direction "C" as shown in FIG. 8) to circumferentially clamp flexible members 254 about the lip 108a of the connecting portion 108. Specifically, as the outer member 260 is rotated, the pin 264 is initially disposed within the unclamped resting portion 253c of the cam slot 253, and then travels through the cam slot 253, namely, the ramp portion 253b, moving the clamping member 250 longitudinally in the distal direction "B." As described above, rotational movement of the clamping member 250 is prevented by the pins 252 of the clamping member 250 interfacing with slots of the connector assembly 240, which forces the clamping member 250 to move longitudinally as the pin 264 of the outer member 260 travels through the cam slot 253 of the clamping member 250.

The transition from the clamped configuration to an unclamped configuration of the drive coupling assembly 210 is substantially similar to the clamping process described above with the exception of the rotation of the outer member 260 in an opposite direction (e.g., counterclockwise direction "D," as shown in FIG. 8). This moves the clamping member 250 in the proximal direction "A" (FIG. 5) as the pin 264 moves in reverse through the cam slot 253, namely, from the clamped resting portion 253a, through the ramp portion 253b, and eventually the unclamped resting portion 253c, to thereby extend flexible arms 254 proximally of the outer member 260.

Once clamping member 250 is unclamped from the lip 108a of the connecting portion 108, the adapter assembly 200 is decoupled from the surgical instrument 100. As the adapter assembly 200 is removed from the surgical instrument 100, the flexible members 254 of the clamping member 250 are initially flexed radially outward (e.g., expanded) by the lip 108a of the connecting portion 108 urging the ramp 258 of the members 254. The flexible members 254 then slide off of or snap past the lip 108a of the connecting portion 108 by the ramp surface 257 contacting the lip 108a as the adapter assembly 200 is removed.

It will be understood that various modifications may be made to the embodiments disclosed herein. For example, the instrument 100 need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

The invention claimed is:

1. A surgical device adapter for coupling an end effector to a handle assembly, the surgical device adapter comprising:
a housing including a proximal end couplable to a distal end of the handle assembly; and
a drive coupling assembly supported on the housing and selectively couplable to the handle assembly, the drive coupling assembly including:
a tubular clamping member having at least one flexible member, the tubular clamping member movable from a proximal position in which the at least one flexible member is disengaged from the distal end of the handle assembly to a distal position in which the at least one flexible member is engaged to the distal end of the handle assembly; and
an outer tubular member defining a longitudinal axis and disposed over the tubular clamping member, the outer tubular member rotatable about the longitudinal axis and relative to the tubular clamping member to move the tubular clamping member between the proximal and distal positions.

2. The surgical device adapter according to claim 1, wherein the housing includes a connector assembly and the tubular clamping member is disposed over the connector assembly.

3. The surgical device adapter according to claim 2, wherein the connector assembly includes at least one longitudinal slot defined in an outer surface thereof, the at least one longitudinal slot configured and dimensioned to interface with at least one first pin projecting from the tubular clamping member.

4. The surgical device adapter according to claim 2, wherein the tubular clamping member includes at least one cam slot configured and dimensioned to interface with at least one second pin projecting from the outer tubular member.

5. The surgical device adapter according to claim 4, wherein rotational movement of the outer tubular member translates the at least one second pin through that at least one cam slot to move the tubular clamping member between the proximal and distal positions.

6. The surgical device adapter according to claim 1, wherein the at least one flexible member includes a proximally-facing ramp surface configured to flex the at least one flexible member upon contacting a lip disposed at the distal end of the handle assembly.

7. A surgical device comprising:
an end effector comprising a first jaw and a second jaw moveable relative to the first jaw;
a handle assembly; and
an adapter assembly removably coupled to a proximal end of the end effector and a distal end of the handle assembly, the adapter assembly comprising:
a housing including a proximal end couplable to the distal end of the handle assembly; and
a drive coupling assembly and selectively couplable to the handle assembly, the drive coupling assembly including:
a tubular clamping member having at least one flexible member, the tubular clamping member movable from a proximal position in which the at least one flexible member is disengaged from the distal end of the handle assembly to a distal position in which the at least one flexible member is engaged to the distal end of the handle assembly; and
an outer tubular member defining a longitudinal axis and disposed over the tubular clamping member, the outer tuber member rotatable about the longitudinal axis and relative to the tubular clamping member to move the tubular clamping member between the proximal and distal positions.

8. The surgical device according to claim 7, the adapter assembly further comprising:
a drive mechanism disposed within the housing and couplable to the handle assembly and the end effector.

9. The surgical device according to claim 7, wherein the housing includes a connector assembly and the tubular clamping member is disposed over the connector assembly.

10. The surgical device according to claim 9, wherein the connector assembly includes at least one longitudinal slot defined in an outer surface thereof, the at least one longitudinal slot configured and dimensioned to interface with at least one first pin projecting from the tubular clamping member.

11. The surgical device adapter according to claim 7, wherein the tubular clamping member includes at least one cam slot configured and dimensioned to interface with at least one second pin projecting from the outer tubular member.

12. The surgical device according to claim 11, wherein rotational movement of the outer tubular member translates the at least one second pin through that at least one cam slot to move the tubular clamping member between the distal and proximal positions.

13. The surgical device according to claim 7, wherein the at least one flexible member includes a proximally-facing ramp surface configured to flex the at least one flexible member upon contacting a lip disposed at the distal end of the handle assembly.

\* \* \* \* \*